Figure 1:
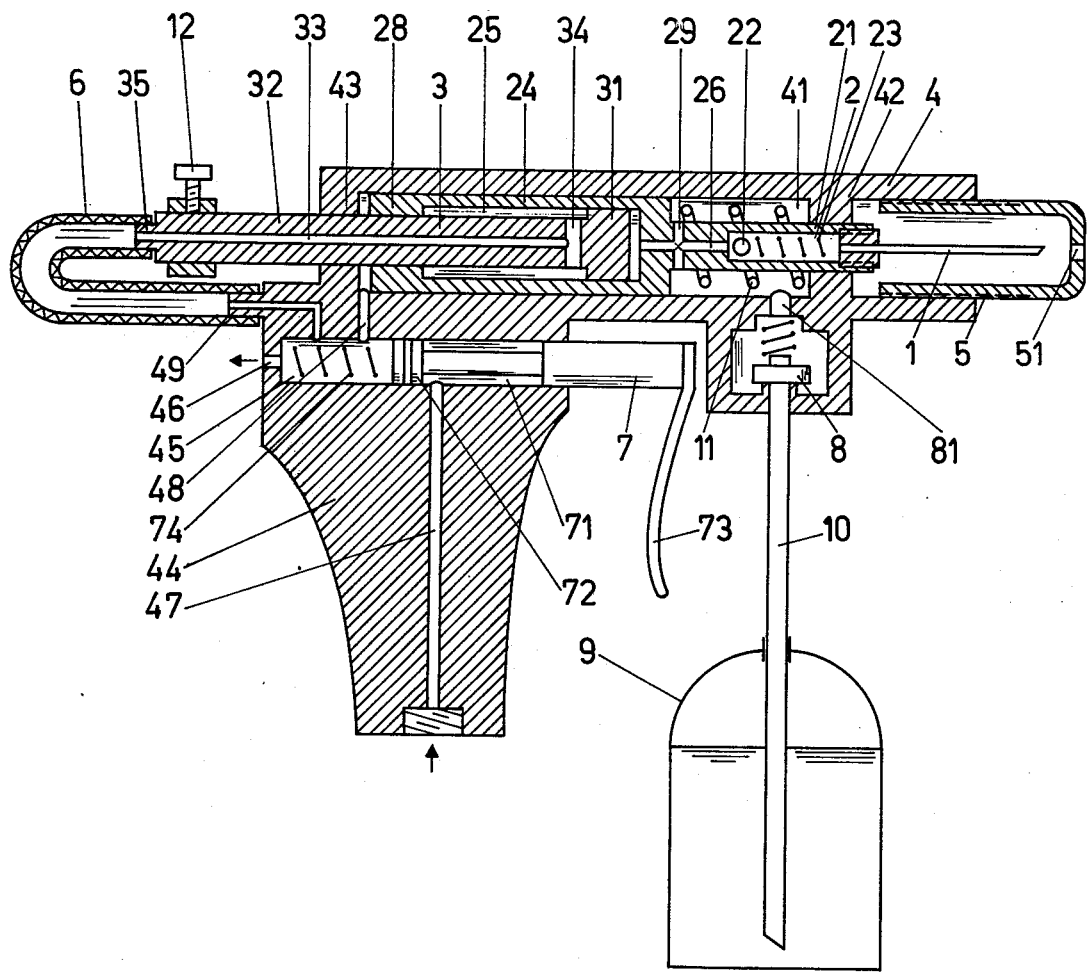

United States Patent

Bron et al.

[11] 4,007,739
[45] Feb. 15, 1977

[54] FLUID-OPERATED HYPODERMIC SYRINGE

[76] Inventors: Dan Bron, 36 Palmah St. Romema, Haifa; Amatzia Arazi, Doar Nah, Medigo, both of Israel

[22] Filed: July 18, 1975

[21] Appl. No.: 596,975

[30] Foreign Application Priority Data

Aug. 2, 1974 Israel ................................ 45391

[52] U.S. Cl. ........................... 128/218 R; 128/216; 222/394
[51] Int. Cl.² .......................................... A61M 5/00
[58] Field of Search ....... 128/218 R, 218 P, 218 A, 128/218 F, 215, 216, 213, 224, 225, 173 H, 172.2, 221; 222/394, 395, 399, 334, 386; 239/303, 337

[56] References Cited

UNITED STATES PATENTS

| | | | |
|---|---|---|---|
| 2,692,706 | 10/1954 | Wiksten | 222/334 X |
| 3,424,154 | 1/1969 | Kinsley | 128/173 H |
| 3,515,130 | 6/1970 | Tsujino | 128/218 R X |
| 3,768,472 | 10/1973 | Hodosh et al. | 128/218 P |

*Primary Examiner*—John D. Yasko
*Attorney, Agent, or Firm*—Toren, McGeady and Stanger

[57] ABSTRACT

A fluid-operated hypodermic syringe for injection of medicinal fluids into livestock, which is adapted to successively and automatically pump out of a container a predetermined quantity of medicinal fluid and to inject it into one animal each. Means are provided to regulate the depth of the needle penetration.

7 Claims, 3 Drawing Figures

FLUID-OPERATED HYPODERMIC SYRINGE

The invention relates to a fluid-pressure operated hypodermic syringe for the injection of medicinal fluids into livestock.

Hypodermic syringes for the injection of medicaments into the body of domestic animals are generally hand-operated, in that the needle is thrust through the skin into the fleshy part and that the plunger for pressing the medicinal fluid through the needle into the animal is moved manually by the fingers of one hand. It has been tried in the past to lighten the work of the person making hundreds or thousands of injections daily and to provide the syringe with built-in pressure means or spring means serving to operate the plunger as well as the needle, however these inventions do not solve the problem of having the container successively filled with the medicament. Other types of syringes are provided with spring means that operate the plunger away from the needle end and serve to fill the cylinder from a large medicament container as soon as the operator releases his grip on the plunger. This requires stronger pressure on the plunger as it has to overcome the resistance of the spring means as well, and it is, therefore, the object of the present invention to provide a hypodermic syringe for continuous operation that requires a minimum of manual effort.

A further object is to provide a protective cover for the needle in retracted position. Still another object is to provide means for controlling the depth of the needle penetration.

The invention consists of a hypodermic syringe for operation by a fluid under pressure which comprises (a) an outer casing having a longitudinal cylindrical hollow space provided with a first port at its "front" or "needle" end for drawing a medicament from a container through a duct and a check-valve, and a second port at its rear end for admitting or releasing pressurized fluid, (b) a front differential piston unit, the large-diameter, rear portion of which is slidingly arranged in the hollow space of the casing, while the small-diameter, front portion protrudes out of the casing through an opening in its front cover and carries an injection needle in its foremost part, the large-diameter portion being furthermore hollow in the shape of a medicament cylinder which is firstly connected to the needle above by a duct containing a check valve, and secondly by at least one opening to a front annular space formed between the casing and the small-diameter portion, (c) pressure means adapted to bias the front differential piston unit to the rear of the casing, (d) a rear differential piston unit having its front portion of larger diameter slidingly arranged in the medicament cylinder of the front differential piston unit, while its rear, longitudinal portion of a smaller diameter penetrates through the rear cover of the medicament cylinder and through the rear of the casing into the open, the latter portion being longitudinally perforated by a fluid duct which at its front end is provided with at least one opening connecting it to the rear annular space formed between the walls of the medicament cylinder and the rear portion of the rear differential piston, (e) manually operated control valve means adapted to primarily admit fluid under pressure to the rear of the front differential piston unit so as to drive the needle forward and to transfer medicament from the front annular space to the medicament cylinder through the openings provided between these spaces and, upon further actuation of the valve, to admit pressurised fluid to the rear annular space so as to drive the rear differential piston unit in forward direction and to eject the medicament through the needle.

In a preferred embodiment of the syringe the pressure means serving to return the front differential piston unit to the rear consist of a helical spring inserted between the casing and the piston unit. In another embodiment the pressure means consist of a fluid under pressure adapted to act on a cylindrical collar projecting from the rear of the front differential piston unit, which is slidingly arranged in a cylindrical chamber of corresponding diameter in the casing.

The valve means are preferably in the shape of a spool valve to be actuated by a trigger, which serves to successively open the access of fluid to the rear of the front and of the rear differential piston unit, respectively.

In a preferred embodiment of the spool valve mechanical or hydraulic pressure means are provided for biasing it against the trigger action; these may consist in a helical spring placed between the rear portion of the spool valve and the valve housing or the valve may be constructed in the shape of a differential piston with the fluid pressure exerting a force in the direction of the larger piston area.

The most suitable fluid for operating the apparatus in respect of ease of handling and non-contamination of the medicament is carbon dioxide which is commercially obtainable in steel flasks.

Figure 3:
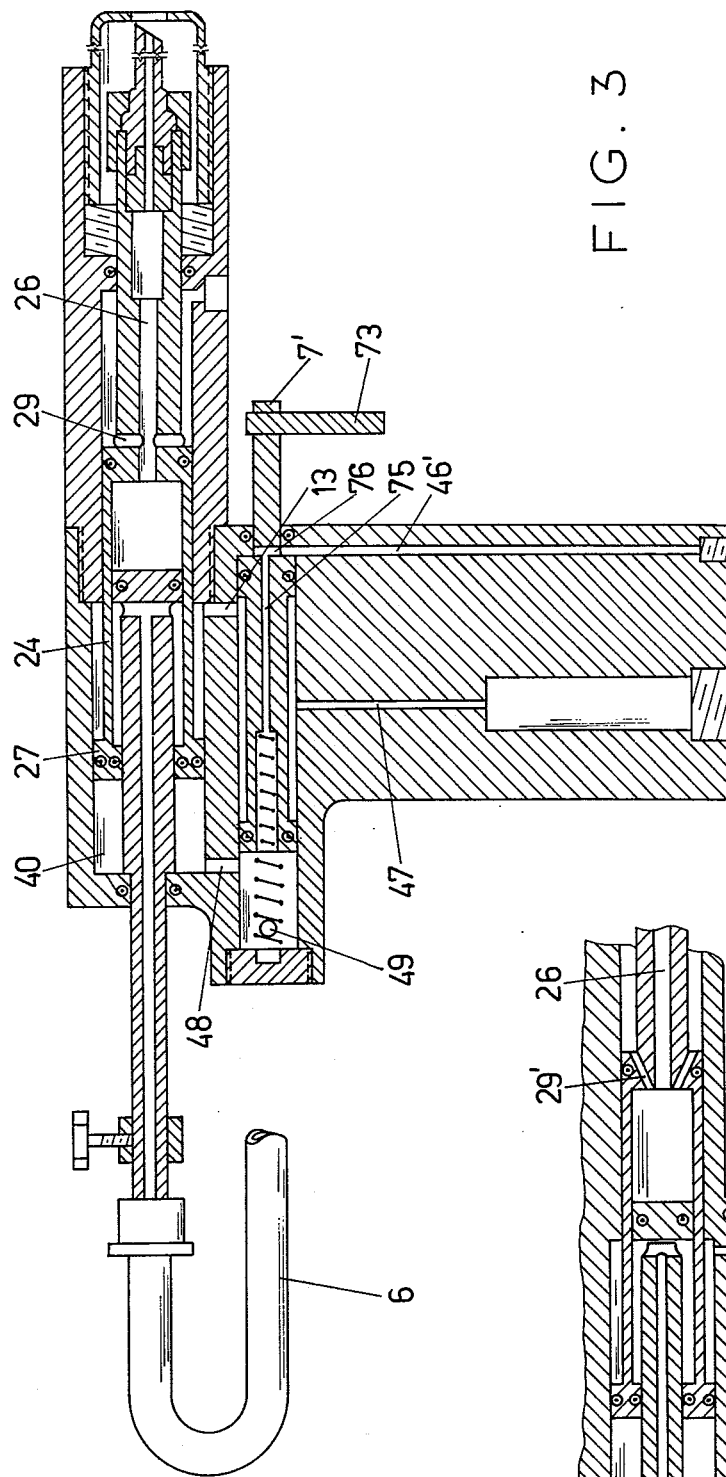
Figure 2:
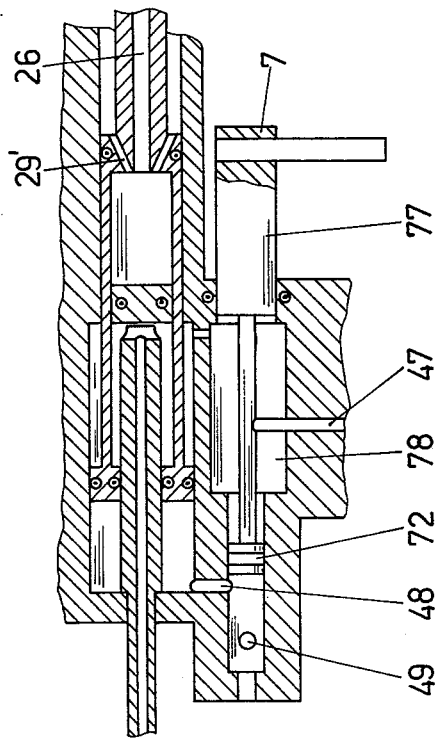

In the accompanying drawings which illustrate, by way of example, three embodiments of the invention, FIG. 1 is a diagrammatic section through a fluid-operated syringe with a spring-operated return motion, and FIG. 2 is a section through an improved embodiment of the invention wherein the movable parts are actuated in forward and backward direction by a fluid under pressure, and FIG. 3 shows a variation of the spool valve and of the ducts in the front differential piston unit.

With a view to facilitate the description and understanding of the drawings the following definitions will be used in the following: the "front" or "needle" end, as appearing on the right side of the drawings, and the "rear" or "grip" end as appearing on the left side of the drawings. Referring now to FIG. 1, an injection needle 1 is rigidly attached to a front differential piston unit 2 which is composed of (1) a cylindrical, hollow front part 21, with its front end provided with internal thread for connection of the needle and containing — in its hollow space — a check valve 22 pressed onto its seat by a weak spring 23, which valve serves to prevent liquid or air from entering into the syringe through the needle, and (2) a larger-diameter cylindrical piston 24 the inner hollow space of which forms a co-axial cylinder 25 destined to receive the medicament, which cylinder is connected to the inner space of the front part by a bore 26 the front end of which forms the seat for the check valve 22. A transverse hole 29 perforates the front part 21 at its rear end adjoining the piston 24 and connects the bore 26 with the annular space. A rear differential piston unit 3 comprises a short front piston 31 of a diameter suitable for sliding in the cylinder 25, and a long rear piston 32 which penetrates through a bore 28 in the rear cover of the cylinder.

The rear piston is hollowed out along its total length by a bore 33 which is connected to the outside of the piston by means of a transverse hole 34; its extreme rear end is formed to a reduced diameter 35 so as to enable its insertion into and connection to, a flexible tube 6. It can be seen that the rear piston unit 3 can move along the total length of the cylinder 25.

The two combined differential piston units are accommodated in a casing 4 the upper part of which is in the shape of a hollow cylinder 41 of a diameter equal to that of the front piston unit, enabling its longitudinal motion therein. The front part 21 — which also carries the needle — passes through a hole in the front cover 42 of the cylinder into a needle cover 5 which latter is screwably fastened into a threaded front portion of the casing 4 and possesses a needle passage 51 in its front. The piston 32 protrudes out of the rear end of the casing through a bore 43. The rear end of the casing is extended downwards to form a grip 44 the upper part of which is drilled in the shape of a cylindrical valve housing 45 with its axis substantially parallel to the cylinder 41, the rear end of this valve housing being open to form an exhaust port 46. Three ports 47, 48 and 49 enter the valve housing, the foremost, inlet duct 47 passing to the bottom of the grip and serving to connect the apparatus to a supply of a fluid under pressure. The second port 48 connects the valve housing with the rear end of the cylinder 41, while the rearmost port 49 connects the rear end of the valve housing with the grip-outside, ending in a nozzle for connecting it to the end of a flexible hose 6.

A spool valve 7 is arranged to be moved inside the valve housing so as to open or close connections between the several ports; it consists of a cylindrical rod recessed (71) approximately over half its length with a short valve piston 72 of the rod diameter formed at the rear end. The front end is attached to a trigger 73 serving to push it to the rear, while a helical spring 74 in the rear of the valve housing counteracts the trigger action and returns the valve to its forward position. The front end of the cylinder 41 is connected to a check valve 8 by means of a port 81, the check valve being, at its lower end, connected to a medicament bottle 9 by means of a vertical tube 10 reaching to the bottom of the bottle.

The helical spring 11 is placed into the front part of the cylinder 41 between its front end and the front end of the piston 24 biasing it towards the rear as long as no fluid pressure acts on this piston.

A movable and adjustable collar 12 is fixed to the outside portion of the rear piston 32, for limiting its forward motion by contact with the casing end.

Before describing the operation of the apparatus it should be noted that the cross-sectional area of the cylinder 25 is substantially equal to the area of the annulus formed between the inside of the casing and the front part 21 of the front differential piston.

The apparatus is connected, at the lower end of the inlet port 47, to a compressed gas cylinder, preferably containing carbon dioxide or to a water supply under pressure.

With the trigger in its foremost position, the rear portion of the inner cylinder 25 is connected to the outside air via hole 34, duct 33, the flexible hose 6, the duct and port 49 and the exhaust port 46. Similarly the rear part of the casing cylinder 41 is at atmospheric pressure, since it is connected to the outside via the ports 48 and 46 respectively. The spring 11 is therefore capable to push the front differential piston unit 2 completely to the rear of the casing, while the position of the rear differential piston 3 is to the front. During the rearward motion the volume of the annular space in front of the casing increases and a certain amount of medicament is drawn from the bottle into this space via the check valve 8. Operation of the trigger 73 moves the spool valve to the rear, whereby the ports 47 and 48 are interconnected through the recessed valve portion and fluid under pressure enters the rear of the casing cylinder 41 driving the movable parts, including the needle, to the front. The latter penetrates the skin of the animal to a depth which can be adjusted by screwing the needle cover 5 in or out of the casing; in the situation shown the needle penetration will be to a maximum depth.

During the forward motion of the front differential piston unit 2 the volume of the annular space in the casing decreases and the medicament contained therein is pressed into the cylinder 25 through the bores 26 and 29, since the check valve 8 prevents return into the bottle, thereby driving the rear differential piston unit to the rear relative to the front piston unit. Owing to the fact — as mentioned above — that the cross sections of the annular space and the cylinder are equal, the total amount of fluid expelled from the annular space is received in the cylindrical space and the position of the rear piston unit does not change relative to the casing. It is obvious that the spring 23 is to be sufficiently strong to counteract the pressure building up in the medicament cylinder during transfer of the medicament and to prevent its ejection through the needle. When the trigger is now pressed further the valve moves to the rear end of the valve housing thus connecting the port 49 with the inlet port 47, pressure reaches the rear annular portion of the rear differential piston 3, driving it in forward direction and ejecting the medicament out of the cylinder 25 through the needle into the animal.

After release of the trigger the piston unit 2 returns to the rear, due to the action of the spring 11, with the rear differential piston unit 3 remaining in its frontal position relative to the front differential piston, until the cycle is repeated by renewed operation of the trigger.

The apparatus shown in FIG. 2 is in many regards identical with that shown in FIG. 1, however it shows constructional details of the parts which enable assembly and dismantling of the movable parts, as well as fluid seals on mutually sliding surfaces. In this Figure reference numbers have been omitted wherever the components coincide or correspond with those in FIG. 1. Furthermore, the medicament bottle (9) as well as the check valve (8) are not shown for clarity's sake. The main difference between the two embodiments is the replacement of the return spring 11 by a hydraulic or pneumatic return mechanism on the one hand, and the placement of the fluid exhaust or drain at the bottom of the grip instead of the exhaust 46 shown in the rear portion of the grip.

The first purpose is served by that the front differential piston is built in three steps, a collar 27 of larger diameter being added at its rear end, and that the casing cylinder is accordingly increased in diameter in its rear portion 40. In order to supply fluid under pressure to the annular space formed between the rear piston 24 and the enlarged cylinder portion, the valve housing 45 is connected to the said annulus by an additional port 13 which, in non-operative position of the spool valve 7 (as in FIG. 2), is connected to the fluid supply duct 47 via the recessed portion 71 of the valve. Fluid pressure acts on the annular portion of the collar 27 and drives it to the rear, there being no counterpressure on this collar, as the rear part of the cylinder 40 is open to the atmosphere. The previously existing exhaust port 46 at the rear of the valve housing is shown to be closed; in its stead an exhaust duct 46' lies in the front part of the grip substantially parallel to the fluid supply duct 47, which is connected to the rear of the spool valve by means of an axial bore 75 in the valve which ends in a transverse bore 76 spilling into the exhaust duct 46'.

This arrangement requires a further modification of the spool valve 7: while in FIG. 1 the total length — except for the recessed portion — is of equal diameter, the present valve has its front part 7' reduced in diameter, whereby an annular space is formed between the valve housing and this front part when the trigger is pressed and the spool valve attains its first position, i.e. the valve piston 72 stops to the rear of the port 48.

Simultaneously connection is made between the exhaust duct 46' and the port 13, permitting the draining of the annular space. In this position of the valve the front differential piston is driven forward as in the aforedescribed example, and after the trigger has been further operated to push the valve completely to the rear, the duct 49 (projecting sideways in this embodiment) is connected to the pressure means which is transmitted, via the flexible hose 6, to the rear piston, driving it forward and ejecting the medicament.

When the trigger is released fluid under pressure is again admitted, via port 13, to drive the front piston unit to the rear, the other spaces being at atmospheric pressure again, so that the cycle can be repeated. Pumping of the medicament out of the bottle and its transfer to the medicament cylinder takes place in the same manner as before.

The advantage of this embodiment over the aforedescribed using a return spring, is that lower fluid pressure can be applied as no forces act in rearward direction, as soon as the pressure is released from the annular space. The fluid advantageously used is carbon dioxide or completely dry compressed air, however water may be used where gases are difficult to obtain. By using an inert gas such as carbon dioxide, the gas escaping through the exhaust duct 46' may be led, through a pipe, to the bottom of the medicament bottle (9) serving to stir the medicine.

FIG. 3 shows the central portion of the apparatus, more especially the spool valve 7 which latter is similar to that shown in FIG. 1 with the exception that the front part 77 is of larger diameter than the rear valve piston 72. The valve housing is enlarged in its central portion to form a hollow cylindrical space 78 which reaches forward as far as the port 13 of FIG. 2, while the fluid inlet 47 connects it permanently to the fluid supply. Since the diameter of the front part 77 is larger than that of the piston 72, the fluid pressure exerts a force in forward direction and presses against the finger operating the trigger 73. In the drawing the valve is shown in its foremost position, held there by stop means which are not visible in the drawing. Similarly as in the embodiment shown in FIG. 2, fluid pressure reaches the rear annular space created between the piston 24 and the casing via the inlet 47, the cylindrical space 78 in the valve housing and the port 13, however in contradistinction to the above embodiment this connection is never interrupted and a permanent pressure in rearward direction is exerted on the front differential piston unit 2.

Only after the port 48 is uncovered by the valve piston 72 and fluid pressure acts on the rear surface of the front piston — which is several times larger than the annular space of the collar 27 — does the unit move to the front, the counterpressure on the collar being comparable in action to that of the helical spring 11 described in conjunction with FIG. 1; however, in the present case the force remains constant, while the spring offers increased resistance with increased compression. In all other respects this spool valve operates similar to that shown in FIG. 2. Another alteration is shown with regard to the inclined holes 29' which replace the perpendicular bore 29 of FIG. 2 and connect the medicament cylinder with the front annular space. This alteration is not essential, however it provides a larger passage for the medicament than the bore 26 shown in FIGS. 1 and 2.

The invention is not limited to the embodiments illustrated and described in the foregoing, but may be modified and improved upon by a person skilled in the art without, however, deviating from the spirit of the invention and the scope of the following claims.

We claim:

1. A hypodermic syringe for operation by a fluid under pressure which comprises (a) an outer casing having a longitudinal cylindrical hollow space provided with a first port at its "front" or "needle" end for drawing a medicament from a container through a duct and a check-valve, and a second port at its rear end for admitting or releasing pressurized fluid, (b) a front differential piston unit, the large-diameter, rear portion of which is slidingly arranged in the hollow space of the casing, while the small-diameter, front portion protrudes out of the casing through an opening in its front cover and carries an injection needle in its foremost part, the large-diameter portion being furthermore hollow in the shape of a cylinder which is firstly connected to the needle by a duct containing a check valve, and secondly by at least one opening to a front annular space formed between the casing and the small-diameter portion, (c) pressure means adapted to bias the front differential piston unit to the rear of the casing, (d) a rear differential piston unit having its front portion of larger diameter slidingly arranged in the medicament cylinder of the front differential piston unit, while its rear, longitudinal portion of a smaller diameter penetrates through the rear cover of the medicament cylinder and through the rear of the casing into the open, the latter portion being longitudinally perforated by a fluid duct which at its front end is provided with at least one opening connecting it to the rear annular space formed between the wall of the medicament cylinder and the rear portion of the rear differential piston, (e) manually operated valve means adapted to primarily admit fluid under pressure to the front differential piston unit so as to drive the needle forward and to transfer medicament from the front annular space to the medicament cylinder through the openings provided between these spaces and, upon further actuation of the valve, to admit pressurized fluid to the rear annular space so as to drive the rear differential piston unit in forward direction and to eject the medicament through the needle.

2. A hypodermic syringe as claimed in claim 1 wherein the pressure means serving to return the front differential piston unit to the rear consists of a helical spring inserted between the casing and the said piston unit.

3. A hypodermic syringe as claimed in claim 1 wherein the pressure means serving to return the front differential piston unit to the rear consist of a fluid under pressure adapted to act on a cylindrical collar projecting out of the rear portion of the front differential piston unit which collar is arranged to move in a cylindrical chamber of corresponding diameter in the rear of the casing.

4. A hypodermic syringe as claimed in claim 1 wherein the valve means are in the shape of a spool valve to be actuated by a trigger, which serves to successively open the access of fluid to the rear of the front differential piston unit and of the rear differential piston unit, respectively.

5. A hypodermic syringe as claimed in claim 4 wherein the spool valve is biased against the trigger action by means of a helical spring placed between the rear portion of the said spool and the valve housing.

6. A hypodermic syringe as claimed in claim 4 wherein the spool valve is biased against the trigger action by fluid pressure acting simultaneously on a piston of larger diameter and an opposed piston of smaller diameter forming part of the spool valve.

7. A hypodermic syringe as claimed in claim 1 operated by carbon dioxide gas under pressure.

* * * * *

UNITED STATES PATENT OFFICE
CERTIFICATE OF CORRECTION

Patent No. 4007739      Dated February 15, 1977

Inventor(s) Dan Bron et al

It is certified that error appears in the above-identified patent and that said Letters Patent are hereby corrected as shown below:

In the heading of the Patent [76] should read as follows:

-- [76] Inventors: Dan Bron, 36 Palmah St. Romema, Haifa;
Amatzia Arazi, Doar Nah, Megido, both of Israel--.

Signed and Sealed this

Third Day of May 1977

[SEAL]

Attest:

RUTH C. MASON
*Attesting Officer*

C. MARSHALL DANN
*Commissioner of Patents and Trademarks*